(12) United States Patent
Pauza et al.

(10) Patent No.: US 8,403,895 B2
(45) Date of Patent: *Mar. 26, 2013

(54) INJECTION OF FIBRIN SEALANT INCLUDING AN ANESTHETIC IN SPINAL APPLICATIONS

(75) Inventors: Kevin Pauza, Tyler, TX (US); Brian D. Burkinshaw, Pflugerville, TX (US); Steven I. Whitlock, Austin, TX (US); Mark I. Richards, Leander, TX (US); James B. Rogan, Austin, TX (US)

(73) Assignee: Spinal Restoration, Inc., Austin, TX (US)

( * ) Notice: Subject to any disclaimer, the term of this patent is extended or adjusted under 35 U.S.C. 154(b) by 219 days.

This patent is subject to a terminal disclaimer.

(21) Appl. No.: 12/587,312

(22) Filed: Oct. 5, 2009

(65) Prior Publication Data

US 2010/0143327 A1 Jun. 10, 2010

Related U.S. Application Data

(62) Division of application No. 11/205,775, filed on Aug. 17, 2005, now Pat. No. 7,597,687.

(60) Provisional application No. 60/623,600, filed on Oct. 29, 2004.

(51) Int. Cl.
  *A61M 5/158* (2006.01)
  *A61M 5/19* (2006.01)
  *A61M 25/06* (2006.01)
  *A61M 5/32* (2006.01)
  *A61B 17/34* (2006.01)

(52) U.S. Cl. ......... 604/264; 604/272; 606/167; 606/185

(58) Field of Classification Search .................. None
See application file for complete search history.

(56) References Cited

U.S. PATENT DOCUMENTS

| | | | |
|---|---|---|---|
| 2,533,004 A | 12/1950 | Ferry et al. |
| 3,089,815 A | 5/1963 | Lieb et al. |
| 3,117,696 A | 1/1964 | Herman |
| 3,223,083 A | 12/1965 | Cobey |
| 3,390,814 A | 7/1968 | Creighton |
| 4,264,305 A | 4/1981 | Rasmussen et al. |
| 4,359,049 A | 11/1982 | Redl et al. |
| 4,370,982 A | 2/1983 | Reilly |
| 4,393,041 A | 7/1983 | Brown et al. |
| 4,394,862 A | 7/1983 | Shim |
| 4,427,650 A | 1/1984 | Stroetmann |
| 4,442,655 A | 4/1984 | Stroetmann |
| 4,447,223 A | 5/1984 | Kaye et al. |
| 4,471,888 A | 9/1984 | Herb |
| 4,610,666 A | 9/1986 | Pizzino |
| 4,619,913 A | 10/1986 | Luck et al. |
| 4,631,055 A | 12/1986 | Redl et al. |
| 4,669,636 A | 6/1987 | Miyata |
| 4,714,457 A | 12/1987 | Alterbaum |
| 4,872,483 A | 10/1989 | Shah |
| 4,874,368 A | 10/1989 | Miller et al. |
| RE33,375 E | 10/1990 | Luck et al. |
| 4,978,336 A | 12/1990 | Capozzi et al. |
| 4,979,942 A | 12/1990 | Wolf et al. |
| 4,998,570 A | 3/1991 | Strong |
| 5,064,098 A | 11/1991 | Hutter et al. |
| 5,080,648 A | 1/1992 | D'Antonio |
| 5,116,315 A | 5/1992 | Capozzi et al. |
| 5,124,155 A | 6/1992 | Reich |
| 5,185,001 A | 2/1993 | Galanakis |
| 5,219,328 A | 6/1993 | Morse et al. |
| 5,259,838 A | 11/1993 | Taylor et al. |
| 5,264,446 A | 11/1993 | Hegasy et al. |
| 5,290,552 A | 3/1994 | Sierra et al. |
| 5,295,614 A | 3/1994 | Chang |
| 5,370,273 A | 12/1994 | Rohloff et al. |
| 5,520,658 A | 5/1996 | Holm |
| 5,582,596 A | 12/1996 | Fukunaga |
| 5,583,114 A | 12/1996 | Barrows et al. |
| 5,585,007 A | 12/1996 | Antanavich et al. |
| 5,631,011 A | 5/1997 | Wadstrom |
| 5,643,192 A | 7/1997 | Hirsh et al. |
| 5,651,982 A | 7/1997 | Marx |
| 5,702,715 A | 12/1997 | Nikolaychik et al. |
| 5,750,657 A | 5/1998 | Edwardson et al. |
| 5,795,571 A | 8/1998 | Cederholm |
| 5,814,066 A | 9/1998 | Spotnitz |
| 5,865,804 A | 2/1999 | Bachynsky |
| 5,925,738 A | 7/1999 | Miekka et al. |
| 5,942,241 A | 8/1999 | Chasin et al. |
| 5,948,384 A | 9/1999 | Filler |

(Continued)

FOREIGN PATENT DOCUMENTS

| | | |
|---|---|---|
| WO | WO81/00516 | 3/1981 |
| WO | WO92/22312 | 12/1992 |

(Continued)

OTHER PUBLICATIONS

US 6,645,204, 11/2003, Sharkey et al. (withdrawn).

(Continued)

*Primary Examiner* — Marsha Tsay
(74) *Attorney, Agent, or Firm* — O'Keefe, Egan, Peterman & Enders LLP

(57) ABSTRACT

A method of treating a disc that is leaking nucleus pulposus through at least one defect in the annulus fibrosus. The method includes injecting a fibrin sealant into the disc to reduce at least a portion of the at least one defect, wherein the fibrin sealant injected into the disc comprises an anesthetic, fibrinogen and an activating compound, wherein at least a portion of the fibrin forms after injection, with the proviso that a corticosteroid is absent from the fibrin sealant injected into the disc.

22 Claims, 4 Drawing Sheets

U.S. PATENT DOCUMENTS

| | | | |
|---|---|---|---|
| 5,962,420 A * | 10/1999 | Edwardson et al. | 514/2.4 |
| 5,980,504 A | 11/1999 | Sharkey et al. | |
| 5,980,866 A | 11/1999 | Uchida et al. | |
| 5,989,215 A | 11/1999 | Delmotte et al. | |
| 6,007,515 A | 12/1999 | Epstein et al. | |
| 6,007,570 A | 12/1999 | Sharkey et al. | |
| 6,007,811 A | 12/1999 | Sawyer et al. | |
| 6,039,741 A | 3/2000 | Meislin | |
| 6,054,122 A | 4/2000 | MacPhee et al. | |
| 6,073,051 A | 6/2000 | Sharkey et al. | |
| 6,079,868 A | 6/2000 | Rydell | |
| 6,095,149 A | 8/2000 | Sharkey et al. | |
| 6,117,425 A | 9/2000 | MacPhee et al. | |
| 6,122,549 A | 9/2000 | Sharkey et al. | |
| 6,124,273 A | 9/2000 | Drohan et al. | |
| 6,126,682 A * | 10/2000 | Sharkey et al. | 607/96 |
| 6,132,396 A | 10/2000 | Antanavich et al. | |
| 6,183,518 B1 | 2/2001 | Ross et al. | |
| 6,197,325 B1 | 3/2001 | MacPhee et al. | |
| 6,224,630 B1 | 5/2001 | Bao et al. | |
| 6,235,041 B1 | 5/2001 | Cheng et al. | |
| 6,258,086 B1 | 7/2001 | Ashley et al. | |
| 6,261,311 B1 | 7/2001 | Sharkey et al. | |
| 6,280,727 B1 | 8/2001 | Prior | |
| 6,320,029 B1 | 11/2001 | Miekka et al. | |
| 6,387,977 B1 | 5/2002 | Sawhney et al. | |
| 6,428,576 B1 | 8/2002 | Haldimann | |
| 6,461,325 B1 | 10/2002 | Delmotte et al. | |
| 6,468,527 B2 | 10/2002 | Austin et al. | |
| 6,471,667 B1 | 10/2002 | Epstein | |
| 6,503,527 B1 | 1/2003 | Whitmore et al. | |
| 6,517,568 B1 | 2/2003 | Sharkey et al. | |
| 6,534,591 B2 | 3/2003 | Rhee et al. | |
| 6,547,810 B1 | 4/2003 | Sharkey et al. | |
| 6,554,851 B1 | 4/2003 | Palasis et al. | |
| 6,559,119 B1 | 5/2003 | Burgess et al. | |
| 6,565,539 B1 | 5/2003 | Zinger et al. | |
| 6,599,272 B1 | 7/2003 | Hjertman et al. | |
| 6,613,324 B1 | 9/2003 | Blomback | |
| 6,620,125 B1 | 9/2003 | Redl | |
| 6,638,276 B2 | 10/2003 | Sharkey et al. | |
| 6,641,562 B1 | 11/2003 | Peterson | |
| 6,648,852 B2 | 11/2003 | Wirt | |
| 6,648,920 B2 | 11/2003 | Ferree | |
| RE38,431 E | 2/2004 | Miekka et al. | |
| 6,695,839 B2 | 2/2004 | Sharkey et al. | |
| 6,723,095 B2 | 4/2004 | Hammerslag | |
| 6,723,335 B1 | 4/2004 | Moehlenbruck | |
| 6,726,685 B2 | 4/2004 | To et al. | |
| 6,733,472 B1 | 5/2004 | Epstein et al. | |
| 6,733,496 B2 | 5/2004 | Sharkey et al. | |
| 6,749,605 B2 | 6/2004 | Ashley et al. | |
| 6,749,617 B1 | 6/2004 | Palasis | |
| 6,762,336 B1 | 7/2004 | MacPhee et al. | |
| 6,764,467 B1 | 7/2004 | Roby et al. | |
| 6,767,347 B2 | 7/2004 | Sharkey et al. | |
| 6,780,411 B2 | 8/2004 | Lewis, Jr. et al. | |
| 6,852,099 B2 | 2/2005 | Redl et al. | |
| 6,874,657 B2 | 4/2005 | Metzner et al. | |
| 6,884,232 B1 | 4/2005 | Hagmann et al. | |
| 6,921,532 B1 | 7/2005 | Austin et al. | |
| 6,972,005 B2 | 12/2005 | Boehm | |
| 7,001,431 B2 | 2/2006 | Bao et al. | |
| 7,004,945 B2 | 2/2006 | Boyd et al. | |
| 7,004,971 B2 | 2/2006 | Serhan et al. | |
| 7,077,865 B2 | 7/2006 | Bao et al. | |
| 7,196,054 B1 | 3/2007 | Drohan et al. | |
| 7,279,001 B2 | 10/2007 | Addis et al. | |
| 7,291,131 B2 | 11/2007 | Call | |
| 7,306,587 B2 | 12/2007 | O'Sullivan et al. | |
| 7,449,019 B2 | 11/2008 | Uchida et al. | |
| 7,507,243 B2 | 3/2009 | Lambrecht et al. | |
| 7,749,273 B2 | 7/2010 | Cauthen, III | |
| 2001/0051834 A1 | 12/2001 | Frondoza et al. | |
| 2002/0004038 A1 | 1/2002 | Baugh et al. | |
| 2002/0045668 A1 | 4/2002 | Dang et al. | |
| 2002/0090725 A1 | 7/2002 | Simpson et al. | |
| 2002/0110544 A1 | 8/2002 | Goldberg et al. | |
| 2002/0110554 A1 | 8/2002 | Lewis, Jr. et al. | |
| 2002/1611335 | 10/2002 | Metzner et al. | |
| 2002/0170926 A1 | 11/2002 | Horner et al. | |
| 2002/0172705 A1 | 11/2002 | Murphy et al. | |
| 2002/0193732 A1 | 12/2002 | Naimark et al. | |
| 2002/0198599 A1 | 12/2002 | Haldimann | |
| 2003/0091558 A1 * | 5/2003 | Woolverton | 424/94.64 |
| 2003/0130617 A1 | 7/2003 | Leone | |
| 2003/0181365 A1 | 9/2003 | Slivka et al. | |
| 2003/0181964 A1 | 9/2003 | Sharkey et al. | |
| 2004/0092864 A1 | 5/2004 | Boehm et al. | |
| 2004/0111136 A1 | 6/2004 | Sharkey et al. | |
| 2004/0127893 A1 | 7/2004 | Hovda | |
| 2004/0191261 A1 | 9/2004 | Redl et al. | |
| 2004/0192658 A1 | 9/2004 | Hunter et al. | |
| 2004/0193151 A1 | 9/2004 | To et al. | |
| 2005/0118156 A1 | 6/2005 | Woolverton | |
| 2005/0119754 A1 | 6/2005 | Trieu et al. | |
| 2005/0152889 A1 | 7/2005 | Austin et al. | |
| 2006/0089646 A1 | 4/2006 | Bonutti | |
| 2006/0095016 A1 | 5/2006 | Pauza et al. | |
| 2006/0106364 A1 | 5/2006 | Whitlock et al. | |
| 2007/0191781 A1 | 8/2007 | Richards et al. | |
| 2007/0213822 A1 | 9/2007 | Trieu | |

FOREIGN PATENT DOCUMENTS

| | | |
|---|---|---|
| WO | WO94/20133 | 9/1994 |
| WO | WO96/17633 | 6/1996 |
| WO | WO97/42986 | 11/1997 |
| WO | WO01/97872 | 12/2001 |

OTHER PUBLICATIONS

Abstract: T. Yagita, "Agent for Controlling Formation of Cheloid at Excision Site for Inflammation Bowel Disease" Feb. 10, 1997; Database WPI, Section Ch, Week 199716, Derwent Publications Ltd., London, GB XP002182938.

Abstract: Sumitomo Cement Co., "Sustained Release Agent for Treatment of Osteomyelitis" Jan. 8, 1993; Database WPI, Section Ch, Week 199306, Derwent Publications Ltd., London, GB XP002182939.

G. Y. Bong et al., "Development of Local Antibiotic Delivery System Using Fibrin Glue" Mar. 1, 1996; Journal of Controlled Release, Elsevier Science Publishers, vol. 29, No. 1, pp. 65-70.

J. Rousou et al., "Randomized Clinical Trial of Fibrin Sealant in Cardiac Surgery Patients Undergoing Resternotomy" Feb. 1989; Journal of Thoracic and Cardiovascular Surgery; vol. 97, No. 2, pp. 194-203.

P. Knoringer, "Fibrin Sealing in Spinal Neurosurgery" 1986.

P.M. McCarthy et al., "Fibrin Sealant: The Cleveland Clinic Experience" 1991.

M. Dahan et al., "The Importance of Biological Glue for the Prevention of Air Leakage in Pulmonary Surgery" 1991; Materials and Methods, pp. 113-116.

H. W. Waclawiczek, "Fibrin Sealing in Liver and Spleen Surgery" 1994.

C. Shaffey et al., "Neurosurgical Applications of Fibrin Glue: Augmentation of Dural Closure in 134 Patients" 1990; Neurosurgery, vol. 26, No. 2, pp. 207-210.

A. Hjortrup, M.D. et al., "Fibrin Adhesive in Perineal Fistulas" Sep. 1991; from the Dept. of Surgical Gastroenterology F, Bispebjerg Hospital and Dept. of Surgical Gastroenterology C, Rigsbospitalet, University of Copenhagen, Copenhagen, Denmark, vol. 34, No. 9.

W. D. Sponitz, M.D. et al., "Clinical Uses of Fibrin Sealant" 1999; Transfusion Therapy: Clinical Principles and Practice, Bethesda, MD: AABB Press.

G. E. Lutz et al., "Flouroscopic Transforaminal Lumbar Epidural Steroids: An Outcome Study" Nov. 1998; Arch Phys Med Rehabil, vol. 79, pp. 18-21.

P. Goupille et al., "The Role of Inflammation in Disk Herniation-Associated Radiculopathy" Aug. 28, 1998; Semin Arthritis Rheum, (1):60-71.

J. D. Kang et al., "Herniated Lumbar Intervertebral Discs Spontaneously Produce Matrix Metalloproteinases, Nitric Oxide, Interleukin-6, and Prostaglandin E2" Feb. 1, 1996; Spine, 21(3): 271-7.

J. S. Saal et al., "High Levels of Inflammatory Phospholipase A2 Activity in Lumbar Disc Herniations" Jul. 1990; Spine, 15(7): 674-8.

O. P. Nygaard et al., "The Inflammatory Properties of Contained and Noncontained Lumbar Disc Herniation" Nov. 1, 1997; Spine, 22(21): 2484-8.

H. Takahashi et al., "Inflammatory Cytokines in the Herniated Disc of the Lumbar Spine" Jan. 15, 1996; Spine, 21(2):218-24.

Product Information, "Celestone Soluspan", brand of betamethasone sodium phosphate and betamethasone acetate Injectable Suspension, USP 6 mg. per mL, Schering Corporation, Kenilworth, N.J. 07033 USA, Rev. Mar. 1996.

Product Information, "Fibrin Sealant Hemaseel APR Kit, Two Component Fibrin Sealant, Vapor Heated, Kit" Manufactured for and Distributed by Haemacure Corp., 2 N. Tamiami Trail, Suite 802, Sarasota, FL 34236, Issued May 1998.

PCT International Search Report, PCT/US05/39277, Jun. 6, 2006.

* cited by examiner

INJECTION OF FIBRIN SEALANT INCLUDING AN ANESTHETIC IN SPINAL APPLICATIONS

This application is a divisional application of U.S. application Ser. No. 11/205,775, filed on Aug. 17, 2005 now U.S. Pat. No. 7,597,687, which claims priority to U.S. provisional application Ser. No. 60/623,600, filed Oct. 29, 2004, incorporated herein by reference.

BACKGROUND OF THE INVENTION

The present invention relates generally to the use of fibrin sealant whereby the sealant is delivered such as by injection to the spinal area, and wherein the sealant includes fibrinogen, thrombin and an anesthetic.

Fibrin sealants, and glues, are well known and are used extensively in various clinical settings. Such sealants are indicated as adjuncts to hemostasis in surgeries when control of bleeding by conventional surgical techniques, including suture, ligature, and cautery is ineffective or impractical. In these cases, the sealant was applied topically.

Recently, fibrin sealant that included a corticosteroid was used to treat disc problems such as fissures in the annulus fibrosus. In this regard, U.S. Pat. No. 6,468,527 discloses that the composition was injected into a disc (an intra-discal injection) to treat disc problems.

SUMMARY OF THE INVENTION

In the practice of the present invention, fibrin sealant is injected into the spinal area of a human being. The sealant comprises fibrinogen and an activating compound such as thrombin, which form fibrin when mixed. The sealant also includes an anesthetic such as a local anesthetic. It has been found that this composition provides surprisingly superior results relative to fibrin sealant compositions containing a corticosteroid. Calcium ions, such as supplied from calcium chloride, may be included in the fibrin sealant. The fibrinogen and/or thrombin may be derived from a freeze-dried component that is reconstituted with a solution containing one or more additives, such as various biological and non-biological agents. However, in one embodiment, corticosteroids are excluded from the fibrin sealant.

In one broad respect, this invention is a method of treating a disc that is leaking nucleus pulposus through at least one defect in the annulus fibrosus, comprising: injecting a fibrin sealant into the disc to reduce at least a portion of the at least one defect, wherein the fibrin sealant injected into the disc comprises fibrinogen, an anesthetic, and an activating compound such as thrombin, wherein at least a portion of the fibrin forms after injection. Optionally, the fibrinogen, the activating compound or both has been reconstituted with a solution containing the anesthetic. In one embodiment, a corticosteroid is absent from the fibrin sealant injected into the disc. This treatment serves to reduce the amount of material from the nucleus fibrosus that leaks through the defect(s) in the annulus fibrosus. The defect can be a tear of the annulus fibrosus, a fissure in the annulus fibrosus, and the like. Advantageously, injection of the fibrin sealant can also serve to restore normal disc height and hydrostatic pressure, a key component. It should be understood that normal physiologic hydrostatic pressure can vary from person to person, and that the treatment may produce near-normal hydrostatic pressure. As used herein, normal physiologic pressure encompasses this range of pressures. In one embodiment, neither the nucleus pulposus nor the annulus fibrosus has been heated in the body to stiffen the disc either prior to or concurrent with the injection, such as discussed in for example U.S. Pat. No. 6,095,149. In one embodiment, in the practice of this invention the nucleus pulposus has not been removed by surgery, such as in the case of a total or partial discectomy or by nucleoplasty for a herniated disc.

In another broad respect, this invention is a method of treating a human back, comprising injecting a fibrin sealant into a disc to seal at least one defect of an annulus fibrosus, wherein the fibrin sealant comprises an anesthetic, fibrinogen and an activating compound such as thrombin, wherein the fibrinogen and thrombin forms at least a portion of the fibrin after injection, and wherein the fibrin sealant does not include a corticosteroid.

In another broad respect, this invention is a method of treating a human back, comprising providing a mixture of an anesthetic, fibrinogen and thrombin within a human disc to treat at least one defect of an annulus fibrosus, and wherein a corticosteroid is absent from the mixture. The mixture may be provided into the disc by injection or otherwise.

This invention also includes a kit including components used to inject the fibrin sealant. The kit may comprise an anesthetic, fibrinogen, such as freeze-dried fibrinogen, thrombin such as freeze-dried thrombin, optionally at least one additive, and a needle for injecting the sealant such as a spinal needle including for example a curved spinal needle. A spinal canula may alternatively be used. The kit excludes corticosteroid. The kit may exclude a device to provide thermal energy to a disc. The kit can optionally include contrast agent and additional additives. A single, dual or multi-barrel syringe, or other fibrin sealant delivery device, may be included in the kit. The fibrin sealant can be delivered using a convention single lumen needle, or through a bilumen or multilumen needle. If a bilumen needle is used, each component can be delivered through a separate lumen. In one embodiment, a bilumen needle or multilumen needle can be used that allows contact of the fibrinogen component and the thrombin component at the tip of the needle. Alternatively, sequential addition of the fibrinogen component followed by injection of the thrombin or other enzyme component can be used, and these injections can occur in the same needle, multiple needles, or in a bilumen or multilumen needle.

In another broad respect, this invention is a process for manufacturing a kit, comprising: providing a fibrinogen component, a thrombin component, an anesthetic component, and a spinal needle or a polymeric catheter or both, wherein the kit excludes corticosteroid and wherein the kit excludes a device to provide thermal energy to a disc.

Advantageously, the method and kit of this invention facilitate extended pain relief for patients with leaky disc syndrome, wherein for example nucleus pulposus leaks out of the disc through defects (e.g. tears or fissures) in the annulus fibrosus. Surprisingly, it has been found that the use of fibrin without corticosteroid provides unexpectedly superior results to injections of fibrin sealant that includes a corticosteroid. The present invention provides unexpectedly superior results to the method set forth in U.S. Pat. No. 6,468,527, which discloses the injection of fibrin sealant containing a corticosteroid. Unexpectedly, fibrin sealant that includes an anesthetic supplies even more superior results. In particular, the fibrin sealant containing an anesthetic provides both immediate and extended pain relief superior to either fibrin sealant with corticosteroid or fibrin sealant that excludes corticosteroid.

DETAILED DESCRIPTION OF THE INVENTION

Figure 1:
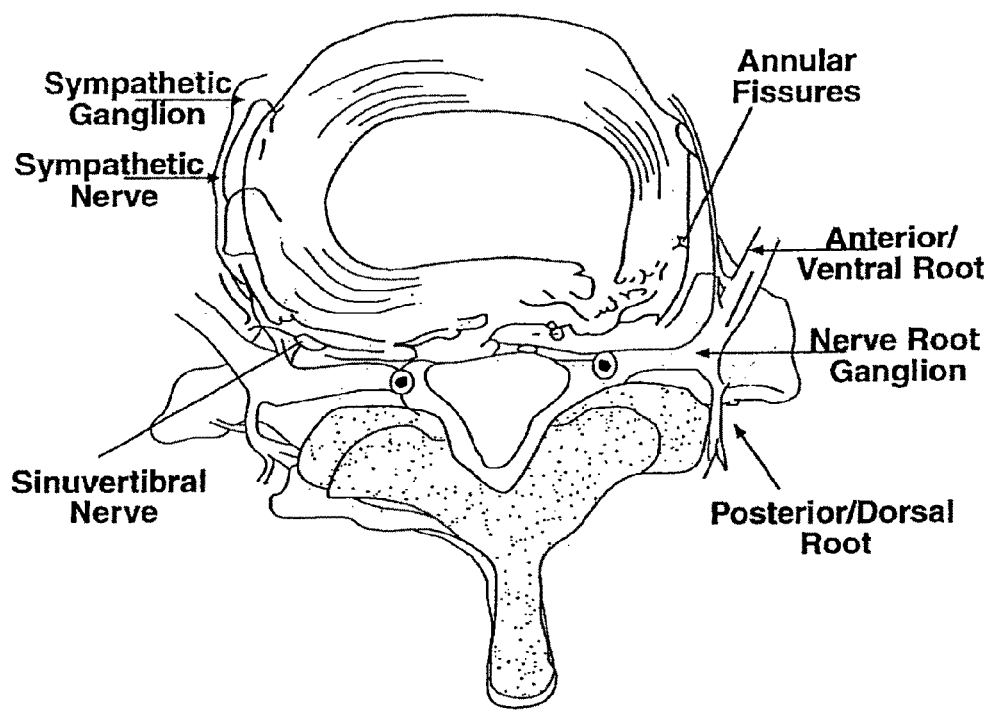
FIG. 1 is a cross-sectional view of a vertebral body at the disk space exhibiting annular fissures which may be treated according to one embodiment of the present invention.
Figure 2:
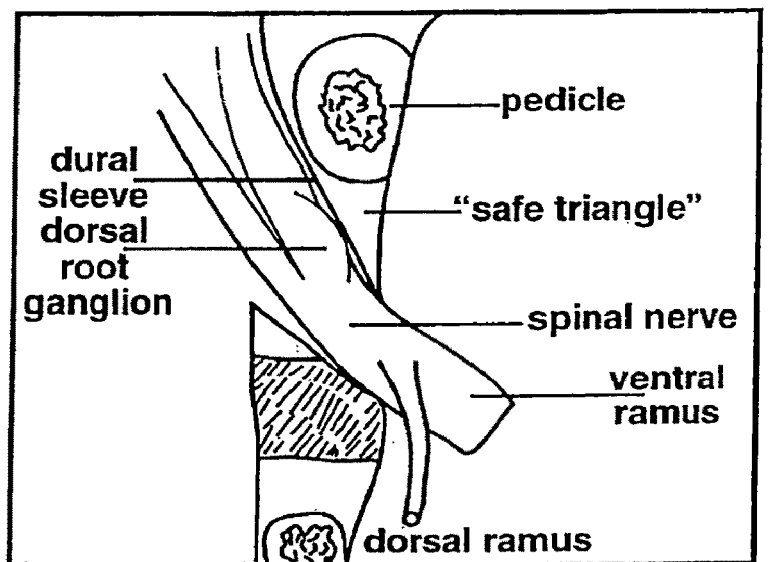
FIG. 2 is a schematic representation of the trans-foraminal space into which the improved sealant may be injected according to one embodiment of the present invention.

The fibrin sealant of the present invention comprises an anesthetic, a fibrinogen component and an activating compounds such as thrombin that converts fibrinogen to fibrin. The sealant optionally contains one or more other additives. Optionally, the fibrinogen, the thrombin, or both is reconstituted with a solution containing at least one of the additives, wherein the additive is other than a corticosteroid. The fibrin sealant is injected into, for example, the disc to seal fissures and tears in the annulus fibrosus. Defects in the annulus fibrosus are commonly diagnosed, currently, using MRI scans and discograms. This can treat both discogenic low back pain and radiculopathy leg pain when injected into the lumbar intervertebral disc.

The fibrinogen used in the practice of this invention includes any fibrinogen that will form fibrin in a human body. Fibrinogen is frequently available in freeze-dried form, and must be reconstituted prior to use. If the thrombin is reconstituted using a solution with an additive, the fibrinogen can also be frozen or fresh, autologous (from the patient to be treated), human including pooled human fibrinogen, recombinant, and bovine or other non-human source such as fish (e.g., salmon and sea trout). The fibrinogen is used in an amount suitable for the given treatment, patient, and so on. Freeze-dried fibrinogen is reconstituted using a solution, typically containing aprotinin and calcium chloride. As discussed herein, either the fibrinogen or thrombin or both is reconstituted with a solution that includes at least one additive. For example, the freeze-dried fibrinogen can be reconstituted using, for example, saline with an anesthetic or an additive, a saline solution containing aprotinin and an anesthetic or an additive, a saline solution containing anesthetic, optionally an additive, and calcium ions ($Ca^{+2}$) such as may be supplied from calcium chloride, or a solution containing combinations of anesthetic and/or additives.

Thrombin is typically the enzyme used which serves to change fibrinogen to fibrin. However, other enzymes can be used such as those derived from snake venom (e.g., batroxobin), or spider venom as is known in the art. As used herein, "activating compound" refers to a compound that causes fibrinogen to form fibrin, and this term includes thrombin, batroxobin, and so on. Thrombin is available commercially, typically in its freeze-dried form. Freeze-dried thrombin must be reconstituted prior to use. The thrombin can also be frozen or fresh. Thrombin can be autologous, from a human or pooled human supply, bovine, fish (such as salmon) or other non-human fibrinogen-cleaving enzyme source such as various arachnids and other venomous species. The thrombin or enzyme is used in any amount which facilitates changing the fibrinogen to fibrin, as is known to one of skill in the art. The thrombin can be reconstituted using saline, optionally containing an anesthetic and/or one or more additives or a saline solution containing an anesthetic and/or an additive, and calcium ions.

In the practice of this invention, the fibrin sealant includes an anesthetic such as a local anesthetic. Representative examples of such local anesthetics include but are not limited to lidocaine HCL (often sold in concentrations of 1.5% or 4%), SARAPIN anesthetic (a sterile aqueous solution of soluble salts and bases from Sarraceniaceae (Pitcher Plant), and bupivacaine HCL (also known as marcaine, which is often sold in concentrations of 0.5% and 0.75%). The chemical name for lidocaine is alpha-diethylaminoaceto-2,6-xylidide, and the IUPAC name is 2-(diethylamino)-N-(2,6-dimethylphenyl)acetamide. The chemical name for bupivicaine is 1-butyl-N-(2,6-dimethylphenyl)-2-piperidinecarboxamide, sometimes referred to as 1-butyl-2',6'-pipecoloxylidide monohydrochloride, having registry number 14252-80-3. Alternatively, procaine (2-diethylaminoethyl 4-aminobenzoate hydrochloride) or other local anesthetic can be employed. Among the local anesthetics, bupivacaine is preferred. In one embodiment, a solution containing about 0.1 to about 10 percent by weight of anesthetic is used. In another embodiment, a about 0.5 to about 5 percent solution is used. The amounts of the solution can vary widely, such as from about 0.1 mL to about 5 mL of the anesthetic solution. More typically, the amount of the anesthetic solution is in the range from about 0.5 to about 2 mL. In general, the amount of anesthetic used is effective to alleviate pain when the sealant is injected or otherwise introduced into the disc. In one embodiment, the anesthetic is water-soluble. In one embodiment, the anesthetic does not contain water-insoluble particles. Combinations of anesthetics can be used. The anesthetic can be injected with the fibrinogen and thrombin, or alternatively one or more of these components can be injected separately, either before or after the fibrin sealant has been injected. The anesthetic can be used in the solutions used to reconstitute the fibrinogen and thrombin (e.g., a solution containing a local anesthetic is used to reconstitute the fibrinogen and a solution containing type II collagen is used to reconstitute the thrombin). Alternatively, the fibrinogen or the thrombin is reconstituted and then the anesthetic is added to the reconstituted fibrinogen or thrombin. Alternatively, the anesthetic can be injected separately, either before or after the fibrin sealant has been injected.

As used herein, the term "additives" means antibiotics; antiproliferative, cytotoxic, and antitumor drugs including chemotherapeutic drugs; analgesic; antiangiogen; antibody; antivirals; cytokines; colony stimulating factors; proteins; chemoattractants; EDTA; histamine; antihistamine; erythropoietin; antifungals; antiparasitic agents; non-corticosteroid anti-inflammatory agents; anticoagulants; analgesics; oncology agents; cardiovascular drugs; vitamins and other nutritional supplements; hormones; glycoproteins; fibronectin; peptides including polypeptides and proteins; interferons; cartilage inducing factors; protease inhibitors; vasoconstrictors, vasodilators, demineralized bone or bone morphogenetic proteins; hormones; lipids; carbohydrates; proteoglycans such as aggrecan (chondrotin sulfate and deratin sulfate), versican, decorin, and biglycan; antiangiogenins; antigens; DBM; hyaluronic acid and salts and derivatives thereof; polysaccharides; cellulose compounds such as methyl cellulose, carboxymethyl cellulose, and hydroxy-propylmethyl cellulose and derivatives thereof; antibodies; gene therapy reagents; genetically altered cells, stem cells including mesenchymal stem cells with transforming growth factor, and/or other cells; cell growth factors to promote rehabilitation of damaged tissue and/or growth of new, healthy tissue such as BMP7 and BMP2; type I and II collagen; collagen hydrolyzate; elastin; sulfated glycosaminoglycan (sGAG), glucosamine sulfate; pH modifiers; methylsulfonylmethane (MSM); osteogenic compounds; osteoconductive compounds; plasminogen; nucleotides; oligonucleotides; polynucleotides; polymers; osteogenic protein 1 (OP-1 including recombinant OP-1); LMP-1 (Lim Mineralization Protein-1); cartilage including autologous cartilage; oxygen-containing components; enzymes such as, for example, peroxidase, which mediate the release of oxygen from such components; melatonin; vitamins; and nutrients such as, for example, glucose or other sugars. However, it is foreseeable that any of these additives may be added to the fibrin sealant separately or in combination. One or more of these additives can be optionally injected with the fibrinogen and thrombin, or alternatively one or more of these components can be injected separately, either before or after the fibrin sealant has been injected. Combinations of these additives can be employed and different additives can be used in the solutions used to reconstitute the fibrinogen and thrombin (e.g., a solution containing a first additive is used to reconstitute the fibrinogen and a solution containing type II collagen is used to reconstitute the thrombin). In addition, one or more other additives can be added to reconstituted solutions of either thrombin or fibrinogen. Likewise, one or more of these additives can be injected with the fibrinogen and activating compound, or alternatively one or more of these additives can be injected separately, either before or after the fibrin sealant has been injected. In one embodiment, the additive is water-soluble. In one embodiment, the additive does not contain water-insoluble particles.

For solutions containing an incompletely water-soluble additive(s), an anti-caking agent such as, for example, polysorbate, may be added to facilitate suspension of this component. Glycol may be inappropriate for use as an anti-caking agent in the instant invention.

It should be appreciated that fibrin formation begins immediately on contact of the fibrinogen and thrombin, such as in the Y-connector of a dual syringe. The term "injecting" of fibrin sealant as used herein thus encompasses any injection of components that form fibrin in the disc, including circumstances where a portion of the components react to form fibrin due to mixing prior to contact with or actual introduction into the disc. It is also within the scope of this invention to sequentially inject the components of the fibrin sealant into the disc, such as by injecting the thrombin component followed by the fibrinogen component, or by injecting the fibrinogen component followed by the thrombin component. Likewise, the fibrinogen component and the thrombin components can be each intermittently injected into the disc.

It should also be appreciated that the point, or points, of injection (e.g., at the tip of a spinal needle) can be within the annulus fibrosus or in the nucleus pulposus. If the injection occurs in the nucleus pulposus, the injected components may form a patch at the interface between the nucleus pulposus and the annulus fibrosus, or, more commonly, the components flow into the defect(s) (e.g., fissures) of the annulus fibrosus and potentially "overflowing" into the interdiscal space. In practice, over-pressurizing the disc by injecting the components into the disc should be avoided.

The anesthetic, fibrinogen and activating compound are injected in amounts effective to seal a given defect of the disc, as is apparent to one of skill in the art. The amount of activating compound such as thrombin can be varied to reduce or lengthen the time to complete fibrin formation. In general, the higher level of thrombin per unit amount of fibrinogen, the faster fibrin formation occurs. If slower fibrin formation is desired, then less thrombin is used per unit fibrinogen. The use of calcium ions (such as from calcium chloride) in one or both of the component solutions will affect the strength of the fibrin so formed, with increasing amount of calcium ions increasing the strength of the fibrin clot. Generally, for a composition comprising fibrinogen that is an aqueous solution, it is believed that from about 3 mL to about 5 mL of such composition is sufficient to be an effective fibrin sealant. However, depending on the use of the composition, the dosage can range from about 0.05 mL to about 40 mL.

Fibrin sealants mimic the final stage of the natural clotting mechanism. Typically, such sealants entail the mixing of a fibrinogen component with an activating enzyme such as thrombin. Thrombin is an enzyme that exists in blood plasma which causes the clotting of blood by converting fibrinogen into fibrin. In normal practice, the components of the fibrin sealant are reconstituted separately, from a freeze-dried state, prior to use. However, use of samples prepared from a frozen state or a fresh state is also acceptable. To increase biocompatibility of the sealant with host tissue, various components may be supplied endogenously from host body fluids. Combining the reconstituted components produces a viscous solution that quickly sets into an elastic coagulum. A method of preparing a conventional fibrin sealant is described by J. Rousou, et al. in Journal of Thoracic and Cardiovascular Surgery, vol. 97, no. 2, pp 194-203, February 1989. Cryoprecipitate derived from source plasma is washed, dissolved in buffer solution, filtered and freeze-dried. The freeze-dried fibrinogen is reconstituted in a fibrinolysis inhibitor solution containing, for example 3000 KIU/ml of aprotinin (a polyvalent protease inhibitor which prevents premature degradation of the formed fibrin), and an additive. The solution is stirred and heated to a temperature of about 37° C. Each solution (the thrombin and fibrinogen solutions) is drawn up in a syringe and mounted on a Y-connector to which a needle is attached for delivery of the combined solution. (See, e.g. the Duploject® device, from ImmunoAG, Vienna, Austria). Thus, mixing of the components only occurs during the delivery process which facilitates clot formation at the desired site of application only. The components should be injected sufficiently quickly to avoid the passage becoming blocked due to fibrin formation in the needle and/or Y-connector.

In one embodiment, the mixing of the fibrin sealant components at least partially occurs in the Y-connector and in the needle mounted on a Y-connector, with the balance of the clotting occurring in the disc. This method of preparation facilitates the formation of a fibrin clot at the desired site in the disc during delivery, or immediately thereafter. Calcium chloride may be included in the fibrin sealant to be injected to modify the composition of the so-formed fibrin and resulting strength of the clot.

In one embodiment, about 75-105 mg/mL of freeze-dried fibrinogen is reconstituted according to conventional methods, and about 45-55 mg/mL thrombin component is reconstituted separately from a freeze-dried state according to the methods and compositions of the present invention. Freeze-dried fibrinogen and freeze-dried thrombin are available in kit-form from such manufacturers as Baxter under names such as TISEEL®. These two fibrin sealant components can be prepared for example in about 2 mL samples each to yield approximately 4 mL of total sealant (reconstituted fibrinogen plus reconstituted thrombin plus anesthetic). Alternatively, about 5 mL of total sealant is used such as where 2 mL samples each of reconstituted fibrinogen and reconstituted thrombin are employed, also with 1 mL of anesthetic to yield approximately 5 mL of total sealant (reconstituted fibrinogen plus reconstituted thrombin plus anesthetic).

While several methods and compositions may be used for preparing the freeze-dried thrombin for use in the invented fibrin sealant, one method is providing about 45-55 mg/mL of freeze-dried thrombin and mixing it with a reconstituting solution. The reconstituting solution for use in reconstituting either the thrombin or fibrinogen, or for both components, may further comprise about 0.1-100 milligrams of another component described herein (e.g., local anesthetic or another additive) and/or calcium chloride. The calcium chloride concentration can be, for example, 1-100 millimoles/mL, and in one embodiment 4-40 millimoles/mL. If employed, the calcium chloride concentration should be sufficient to further the polymerization reaction that forms a durable fibrin sealant clot. A preservative-free reconstituting solution may be desirable, but is not required.

A contrast agent may be used in conjunction with the injection of the fibrin sealant. The contrast agent may be injected prior to injection of the fibrin sealant. Alternatively, the contrast agent is included in the fibrinogen component or thrombin component that is injected into the disc. Contrast agents and their use are well known to one of skill in the art.

Alternative amounts and concentrations of fibrinogen and thrombin may be used to form the desired fibrin sealant clot in the body. For example, as discussed above, varying the fibrinogen and/or thrombin amount/concentration may be done to vary the viscosity and the "setting time" of the combined fibrinogen and thrombin components. Likewise, varying fibrinogen may change the density of the combined components, which may be important for controlling flow through a long conduit such as a catheter into the body. Varying thrombin may vary the polymerization time of the components, which may be important for controlling the time at which the clot forms for ensuring the components set-up at the proper site and time in the body rather than setting-up prematurely.

When acquired in freeze-dried form, the thrombin and fibrinogen need to be reconstituted for use. The thrombin reconstituting solution (e.g., a saline based solution), optionally containing anesthetic and/or one or more additives, can be prepared in a single vial prior to mixing with the freeze-dried thrombin. This component of the fibrin sealant may then be provided to users in a reconstituted state, or in two uncombined vials containing freeze-dried thrombin and a premixed reconstitution solution. Mixing of the contents of the two vials may be performed at any point up to, and including, the time at which the fibrin sealant (or its components) is injected into the patient. Reconstitution of the fibrinogen solution can be accomplished according to conventional methods. For example, the fibrinogen component may be reconstituted in an aprotinin saline solution which optionally contains other components such as, for example, a local anesthetic. If desired, the thrombin or the fibrinogen or both can be reconstituted using a saline solution that contains one or more additives. All solutions are brought to a temperature of about 37° C. Preferably, the thrombin is combined with the fibrinogen solution using the dual-syringe injection procedure described herein to form a single sealant composition which is injected into a patient. The instant invention provides a vehicle for the delivery of the sealant that conveys the sealant to the precise area of the back, seals any annular fissures, and holds the fibrin in place via the elastic coagulum. In addition, the biodegradable nature of the formed fibrin clot minimizes or eliminates the need for invasive surgical removal following the effective period of use. Therefore, an advantage of the sealant and method of application is the ability to provide a minimally invasive means of accomplishing localized, prolonged sealing of defects (e.g., fissures) in the annulus fibrosus, and if an additive is in the sealant, time-released additive delivery. Likewise, the anesthetic provides rapid, temporary pain relieve with long term pain relief arising from the effect of the fibrin sealant.

The fibrin sealant may be injected into the disc or other body area using procedures well known to one skilled in the art. Typically, an introducer needle is inserted into the intradiscal space with the tip being positioned close to the defect in the annulus fibrosus. A finer gauge needle (made of, e.g., stainless steel and capable of puncturing the annulus fibrosus) is then inserted into the introducer needle. The fibrin sealant is injected through the finer gauge needle. Alternatively, a catheter made from a synthetic polymer can be used. With either a finer gauge needle or a catheter made of synthetic polymer, the needle or catheter can be advanced through the introducer needle and into the nucleus pulposus. Alternatively, the needle or catheter can be advanced up to the tip of the introducer needle, but not far as to go beyond the tip of the introducer needle. This can have the advantage of precisely positioning the point of injection, particularly since a polymeric catheter could bend in the nucleus propulsus thereby become mis-positioned. Likewise by positioning the introducer needle at the desired point of injection as an initial matter, the fibrin sealant can be injected quickly to expedite the procedure, which is a benefit to the patient. In general, the fibrin sealant of this invention is injected into the disc, the epidural space, the zygaphysical (2-joint) joint, the vertebral canal, and/or thecal sac. With respect to an injection of fibrin sealant into a disc, an intra-discal injection serves to create a fibrin matrix which seals the disc from leaking material from the nucleus into the area outside the disc. For example, the fibrin sealant can be delivered by fluoroscopic transforaminal lumber epidural or intra-discal injection, such as described in U.S. Pat. No. 6,468,527. For the treatment of back injuries such as these, the fibrin sealant is injected into the nucleus pulposus, shown in FIG. 1, to fill any fissures or voids of the annulus fibrosus, to seal the bone end plates to the disc, increase pressure of the disc, and to increase the height of the disc space. In general, the fibrin sealant is injected at a location near the defect in the annulus fibrosus. Typically the fibrin sealant will flow into the fissures in the annulus fibrosus, and some fibrin sealant may thus flow out of the intradiscal space. The injection may also serve to coat areas adjacent to the disc, directly on the nerve roots and surrounding areas which serve to protect those areas from the effects of the leaking nucleus material. Sealing the fissures and bone end plates halts the leakage of harmful chemicals into the disc environment and prevents the initiation of foreign-body reactions towards the damaged disc by the immune system. Increasing the disc space relieves pressure on the nerve root. That is, as a result of the injection, an increase of the disc height occurs, which increases the spacing between lamina, and which in turn relieves pressure on the nerve roots on the lamina. For this application, supplementation of the fibrin sealant with growth factors may promote rehabilitation of the damaged tissues or the gradual replacement of the fibrin sealant with healthy tissue.

Use of the improved fibrin sealant composition may be better understood by reference to the following examples. These examples are representative and should not be construed to limit the scope of this invention or claims hereof. Unless otherwise indicated (example 3), corticosteroid is absent from the fibrin sealant being used in these examples and the procedures were conducted in the absence of a heating step of the nucleus fibrosus and annulus fibrosus and in the absence of a partial or total discectomy.

Example 1

Fluoroscopic Transforaminal Epidural Injection

With a patient in the prone position on the imaging table, a fluoroscope is positioned and adjusted to locate the intervertebral foramen of the affected nerve root. A curved 22 ga.× 3.5" needle is introduced after anesthetizing the skin and deep tissue. The needle is advanced under direct fluoroscopic vision to a position in the anterior epidural space. Positioning of the needle is verified by a lateral fluoroscopic view and by injecting contrast medium through the needle. Such positioning may or may not require further adjustment. If adjusted, location of the needle is once again verified. Advancement of the needle into the correct region may stimulate pain in a manner consistent with the initial complaint. Therefore, needle placement may also be verified by the patient's pain recognition. The epidural space is anesthetized with injectable anesthetic. The fibrin sealant of fibrinogen and thrombin (prior to clotting) is then introduced through the needle with continuous gentle pressure until the volumes of the dual syringe system are sufficiently depleted. The thrombin or fibrinogen or both has been reconstituted with a solution containing at least one additive. The fibrin sealant then coats the nerve root and annulus and the needle is withdrawn. Patient observation and vital signs monitoring is performed for about 20-30 minutes following the procedure.

For this procedure, a sufficient volume of the fibrin sealant is injected to effectively hydro-dissect the area around the targeted nerve root. It is believed that due to the avascular nature of the epidural space, the absorption/degradation period is typically longer than that observed for open applications in regions with greater vascularity and exposure to room air at the time of application.

The ability of the fibrin sealant to seal annular fissures related to disc herniation offers a therapeutic benefit to patients. Chemical radiculitis, or inflammation of the nerve root, is known to be quite painful in some instances. It is believed that use of the fibrin sealant in the above described manner not only coats the nerve root, but also seals annular fissures surrounding the herniated disk. (See FIG. 1). As a result of the hydro-dissection of the area around the affected nerve root, the sealant also seals annular fissures from outside the annulus.

Example 2

Fluoroscopic Guided Intra-Discal Injection

After sterile preparation, an introducer needle is advanced in oblique projection to a superior articular process. A curved spinal needle is advanced through the introducer needle into the disc. Both anterior-posterior and lateral fluoroscopic projections are used to confirm proper needle placement. If the needle placement needs to be adjusted, placement is again confirmed fluoroscopically. A contrast agent is injected to confirm needle placement. In patients with chemical radiculitis, the contrast agent can be observed to be leaking through the annular fissures and/or intra-discal pathology can be identified. Once the needle is properly positioned in the intra-discal space, the fibrin sealant (or its components) is injected. The thrombin or fibrinogen or both has been reconstituted with a solution containing at least one additive. The fibrin sealant is observed to force the contrast agent from the intra-discal space as it seals the annual fissures. Alternatively, the contrast agent is injected with the sealant. Alternatively, no contrast agent is used. The procedure seals the defects/fissures of the annulus fibrosus and stops the chemical leakage and facilitates regeneration within the disc.

Example 3

Figure 3:
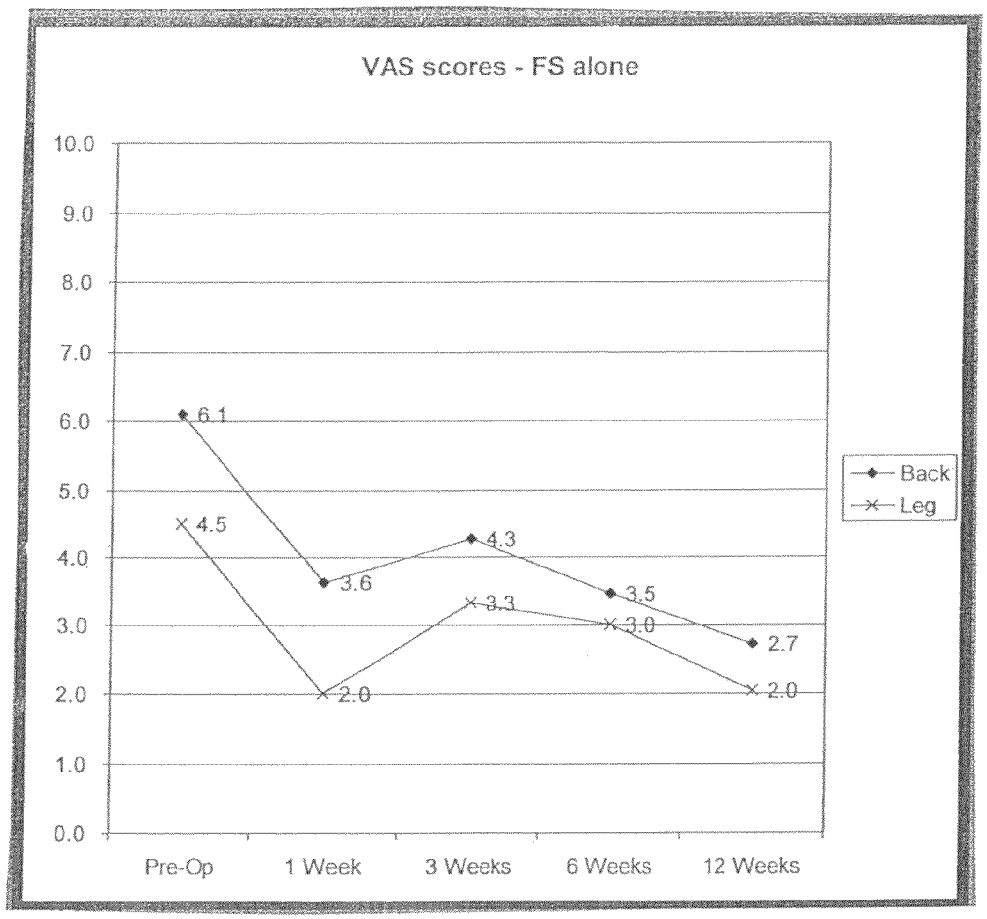
FIGS. 3 and 4 show graphs of the VAS scores from example 3.
Figure 4:
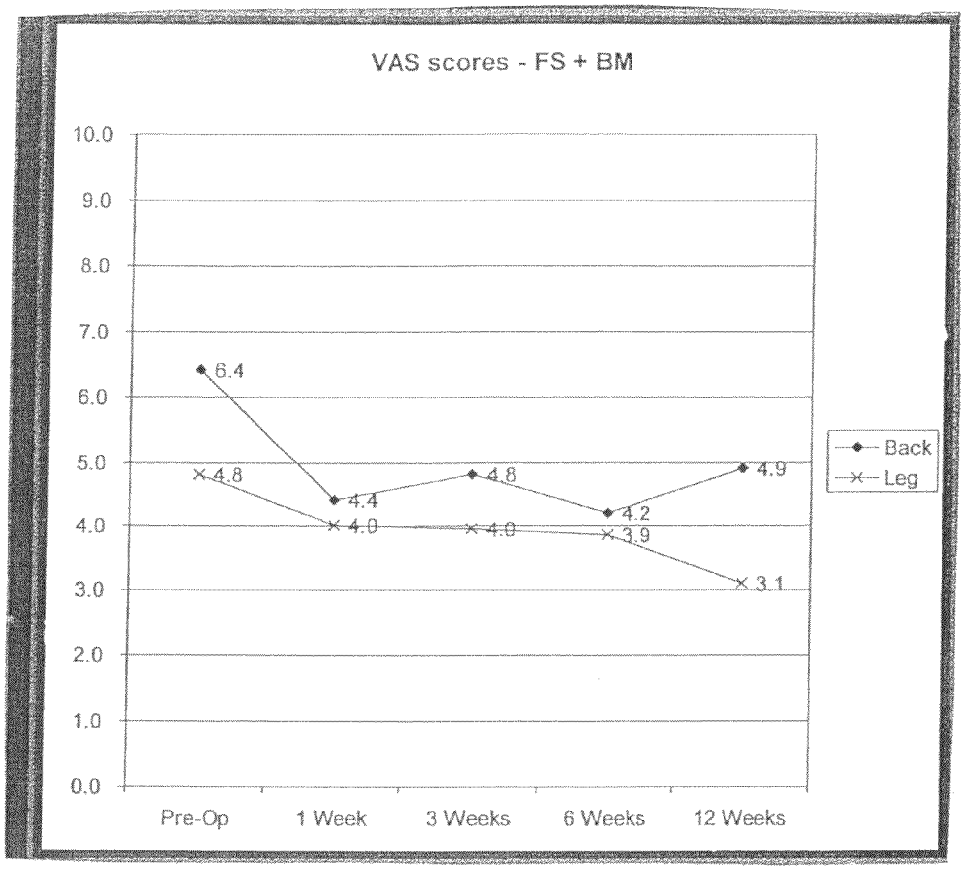

Comparison of Injection of Fibrin Sealant to Injection of Fibrin Sealant Containing a Corticosteriod Twenty patients were split into two 10-patient groups. All of the patients suffered from pain due to disc degeneration caused by defects (fissures) in the annulus fibrosus. All of the patients had previously failed at least 6 months of traditional conservative therapy. Using the procedure in example 2, the first group of patients was intra-discally injected with fibrin sealant containing fibrinogen and thrombin. Using the procedure in example 2, the second group of patients was intra-discally injected with fibrin sealant containing fibrinogen, thrombin, and betamethasone (a corticosteroid). The corticosteroid was in the thrombin component. Each patient rated back and leg pain on a scale of 0 to 10, before and at pre-defined intervals following surgery. The results (VAS scores) are shown in FIGS. 3 and 4. As can be seen, the patients that were injected with fibrin sealant alone (without betamethasone) experienced superior pain relief to those patients that were injected with fibrin sealant containing betamethasone. It had been anticipated that the patients receiving injections that included betamethasone would experience superior results due to the action of the betamethasone to reduce inflammation. However, the opposite was observed. Indeed, the patients injected with fibrin sealant only experienced significantly improved pain relief, not only after one week from surgery, but especially 12 weeks after surgery. These results were surprising and unexpected.

Example 4

Fibrin Sealant Including Local Anesthetic

Using the procedure of example 2, patients were intra-discally injected with fibrin sealant containing fibrinogen, thrombin, and a local anesthetic (bupivacaine HCL). The local anesthetic solution (approximately 1 mL) was mixed into a calcium chloride solution used to reconstitute the fibrinogen. The total amount of fibrin sealant injected was thus 5 mL. It was found, surprisingly, that the fibrin sealant including a local anesthetic provided superior results to either fibrin sealant containing a corticosteroid or the fibrin sealant of example 3.

Example 5

Fibrin Sealant with a Local Anesthetic

A patient was treated with fibrin sealant containing a local anesthetic. The local anesthetic was used to reconstitute the thrombin. The patient suffered from pain due to disc degeneration caused by defects (fissures) in the annulus fibrosus. Using the procedure in example 2, the patient was intra-discally injected with fibrin sealant containing fibrinogen, thrombin, and a local anesthetic (3 cc of 0.75% bupivacaine). Local anesthetic was used, reconstitute the thrombin. A total of 5 cc of fibrinogen, thrombin, and local anesthetic was injected. The patient rated back and leg pain on a scale of 0 to 10, before and at predefined intervals following surgery. The results were as follows for back pain: pre-treatment, 4; 1 week after treatment, 4, 3 weeks after treatment, 1; and after 6 weeks, 1. Leg pain was zero both at pre-treatment and after treatment. Owing to the dramatic decrease in pain after 6 weeks, these results were surprising and unexpected.

It is envisioned that the present invention may be used to address various conditions through use of the fibrin sealant in a manner similar to that described in the examples above. Discussion of this invention referenced particular means, materials and embodiments elaborating limited application of the claimed invention. The invention is not limited to these particulars and applies to all equivalents. Although this invention has been described above with reference to particular means, materials and embodiments, it is to be understood that the invention is not limited to these disclosed particulars, but extends instead to all equivalents within the scope of the following claims.

What is claimed is:

1. A method of treating a disc that is leaking nucleus pulposus through at least one defect in the annulus fibrosus, comprising:
   inserting a first needle having a tip by piercing the annulus fibrosus and pushing the first needle tip into the nucleus pulposus,
   inserting a polymeric catheter or a second needle into the first needle up to but not beyond the tip of the first needle,
   then injecting a fibrin sealant through the polymeric catheter or second needle, or both the first needle and the polymeric catheter or second needle, into the disc to reduce at least a portion of the at least one defect, wherein the fibrin sealant injected into the disc comprises an anesthetic, fibrinogen and an activating compound, wherein at least a portion of the fibrin forms after injection, with the proviso that a corticosteroid is absent from the fibrin sealant injected into the disc.

2. The method of claim 1, with the proviso that neither the nucleus pulposus nor the annulus fibrosus has been heated.

3. The method of claim 1, wherein the fibrin sealant consists essentially of fibrinogen, the activating compound and the anesthetic, optionally at least one additive, and optionally calcium chloride.

4. The method of claim 1, wherein the fibrin sealant consists of fibrinogen, an activating compound and the anesthetic, optionally the at least one additive, and optionally containing calcium chloride.

5. The method of claim 1, wherein calcium chloride is injected with the fibrinogen and the activating compound.

6. The method of claim 1, wherein the activating compound is thrombin.

7. The method of claim 1, wherein the anesthetic is lidocaine, sarapin or bupivicaine.

8. The method of claim 1, wherein at least one additive is also injected.

9. The method of claim 1, wherein no portion of the nucleus pulposus has been removed by surgery.

10. The method of claim 1, wherein the at least one defect is a tear or fissure in the annulus fibrosus.

11. The method of claim 1, wherein normal hydrostatic pressure in the disc is restored.

12. The method of claim 1, wherein normal disc height is restored.

13. The method of claim 1, wherein the fibrinogen is autologous.

14. The method of claim 1, wherein the injection is performed using a dual barrel syringe.

15. The method of claim 1, wherein the activating compound is thrombin, and wherein a mixture of anesthetic, fibrinogen and thrombin is injected.

16. The method of claim 1, wherein the activating compound is thrombin, and wherein the fibrinogen and thrombin are injected sequentially and at least partially mix in the disc.

17. The method of claim 1, wherein the anesthetic is injected sequentially either before, with or after the fibrinogen and thrombin and at least partially mix in the disc.

18. The method of claim 1, wherein the disc is injected with the fibrin sealant at multiple points.

19. The method of claim 1, wherein the disc is a lumbar disc.

20. The method of claim 1, wherein the disc is a cervical disc.

21. The method of claim 1, wherein the disc is a thoracic disc.

22. The method of claim 1, wherein a contrast agent is injected either before the fibrin sealant, with the fibrin sealant, or after the fibrin sealant has been injected.

* * * * *